US012796949B2

(12) United States Patent
Kanoun et al.

(10) Patent No.: US 12,796,949 B2
(45) Date of Patent: Nov. 17, 2026

(54) SENSOR READOUT CIRCUIT AND METHOD

(71) Applicant: SEMICONDUCTOR COMPONENTS INDUSTRIES, LLC, Phoenix, AZ (US)

(72) Inventors: Moez Kanoun, Waterloo (CA); Abdullah Ahmed, Scarborough (CA); Jonas Weiland, Del Mar, CA (US); Alexander Heubi, La Chaux-de-Fonds (CH)

(73) Assignee: SEMICONDUCTOR COMPONENTS INDUSTRIES, LLC, Scottsdale, AZ (US)

( * ) Notice: Subject to any disclaimer, the term of this patent is extended or adjusted under 35 U.S.C. 154(b) by 948 days.

(21) Appl. No.: 17/820,960

(22) Filed: Aug. 19, 2022

(65) Prior Publication Data

US 2023/0284926 A1 Sep. 14, 2023

Related U.S. Application Data

(60) Provisional application No. 63/269,052, filed on Mar. 9, 2022.

(51) Int. Cl.
*A61B 5/0537* (2021.01)
*A61B 5/00* (2006.01)
(Continued)

(52) U.S. Cl.
CPC ........ *A61B 5/0537* (2013.01); *A61B 5/14532* (2013.01); *A61B 5/725* (2013.01); *H03F 3/08* (2013.01)

(58) Field of Classification Search
CPC ... A61B 5/0537; A61B 5/14532; A61B 5/725; A61B 5/7225; H03F 3/08;
(Continued)

(56) References Cited

U.S. PATENT DOCUMENTS

2016/0112037 A1* 4/2016 Lyden .................... H03K 5/003 327/307
2017/0067848 A1 3/2017 Chandrasekhar et al.
(Continued)

OTHER PUBLICATIONS

Yanez, Miriam Garcia, "Glucose Meter Fundamentals and Design," Freescale Semiconductor, Document No. AN4364, Rev. 1, Jan. 2013.
(Continued)

*Primary Examiner* — Jessica Han
*Assistant Examiner* — Jose E Pinero
(74) *Attorney, Agent, or Firm* — Paul J. Polansky

(57) ABSTRACT

A sensor circuit includes a transimpedance amplifier, a feedback network, and a readout circuit. The transimpedance amplifier has a first input for receiving a measured signal, a second input for receiving a reference signal, and an output. The feedback network includes a capacitor and a variable resistor each coupled between the output and the first input of the transimpedance amplifier. The readout circuit is coupled to the feedback network and has an output for providing a readout signal. In a conversion mode, the readout circuit provides the readout signal based on one sample of the output of the transimpedance amplifier. In an integration mode, the readout circuit provides the readout signal based on a plurality of samples of the output of the transimpedance amplifier.

21 Claims, 2 Drawing Sheets

(51) Int. Cl.
*A61B 5/145* (2006.01)
*H03F 3/08* (2006.01)

(58) Field of Classification Search
CPC ......... H03F 2200/129; H03F 2200/144; H03F 2203/45512; H03F 2203/45526; H03F 2203/45528; H03F 3/187; H03F 3/38; H03F 1/32; H03F 3/45475
USPC .............................................................. 330/9
See application file for complete search history.

(56) References Cited

U.S. PATENT DOCUMENTS

| | | | | |
|---|---|---|---|---|
| 2020/0212854 | A1* | 7/2020 | Seyed Aliroteh | G01S 17/10 |
| 2021/0358895 | A1* | 11/2021 | Odabaee | H02M 1/009 |
| 2023/0188100 | A1* | 6/2023 | Fisher | H03F 3/193<br>330/277 |

OTHER PUBLICATIONS

Chang et al., "Highly Integrated Watch for Noninvasive Continual Glucose Monitoring," Microsystems & Nanoengineering, 2022.
Jafari et al., "Chopper-Stabilized Bidirectional Current Acquisition Circuits for Electrochemical Amperometric Biosensors," IEEE Transactions on Circuits and Systems, vol. 60, No. 5, May 2013.
Gonzales et al., "The Progress of Glucose Monitoring—A Review of Invasive to Minimally and Non-Invasive Techniques, Devices and Sensors," Feb. 15, 2019.

* cited by examiner

SENSOR READOUT CIRCUIT AND METHOD

This application claims the benefit of U.S. Provisional Patent Application No. 63/269,052, filed on Mar. 9, 2022, the entire contents of which are incorporated herein by reference.

FIELD OF THE DISCLOSURE

This disclosure relates generally to measurement circuits, and more specifically to sensor circuits useful with electrochemical sensors and the like.

BACKGROUND

Modern electronics have enabled the use of various health-related devices that allow people to live better. One such device is a continuous glucose monitor (CGM). The CGM automatically tracks blood glucose levels, also called blood sugar, throughout the day and night.

The CGM provides the ability to monitor glucose levels of a patient that who is diabetic to make sure that his or her insulin levels are well-regulated. A typical CGM device uses a patch on the body and a readout circuit that takes periodic measurements of the resistivity of tissue. This technique leverages the property that when the body manufactures a large amount of insulin, the resistivity of the interstitial tissue decreases due to a higher level of electrolytes.

A typical CGM circuit uses a readout circuit that biases an electrochemical cell by setting a constant (DC) voltage and measuring the generated current that is proportional to the glucose concentration. CGM products different types of electrochemical cells. Each of them has its own particular characteristics, such as the required DC bias voltage and the range of current measured. The measured current could range from few pico-Amperes (pA) to several micro-Amperes (μA) depending on the type of electrochemical cell. This large range of measurement makes it difficult for a single CGM readout circuit to accommodate all CGM electrochemical cells.

There are at least two known types of CGM readout circuits. The first type uses a current mode approach with a feedback amplifier and current mirrors. The second type uses a voltage mode approach with a transimpedance amplifier (TIA) to convert the current of the sensor into a voltage. The current mode approach has the ability to measure bidirectional currents (source/sink current from the active or "work" electrode) by adding an offset current at its input. However, the current mode approach can increase noise and requires further calibration to cancel the introduced offset. The voltage mode approach can also have an inherent voltage offset error as well as conversion non-linearity and temperature drift. Thus, conventional voltage mode CGM readout circuits have not heretofore been able to fully realize the benefits of operating in the voltage domain.

BRIEF DESCRIPTION OF THE DRAWINGS

The present disclosure may be better understood, and its numerous features and advantages made apparent to those skilled in the art by referencing the accompanying drawings, in which.

The use of the same reference symbols in different drawings indicates similar or identical items. Unless otherwise noted, the word "coupled" and its associated verb forms include both direct connection and indirect electrical connection by means known in the art, and unless otherwise noted any description of direct connection implies alternate embodiments using suitable forms of indirect electrical connection as well.

DETAILED DESCRIPTION

Figure 1:
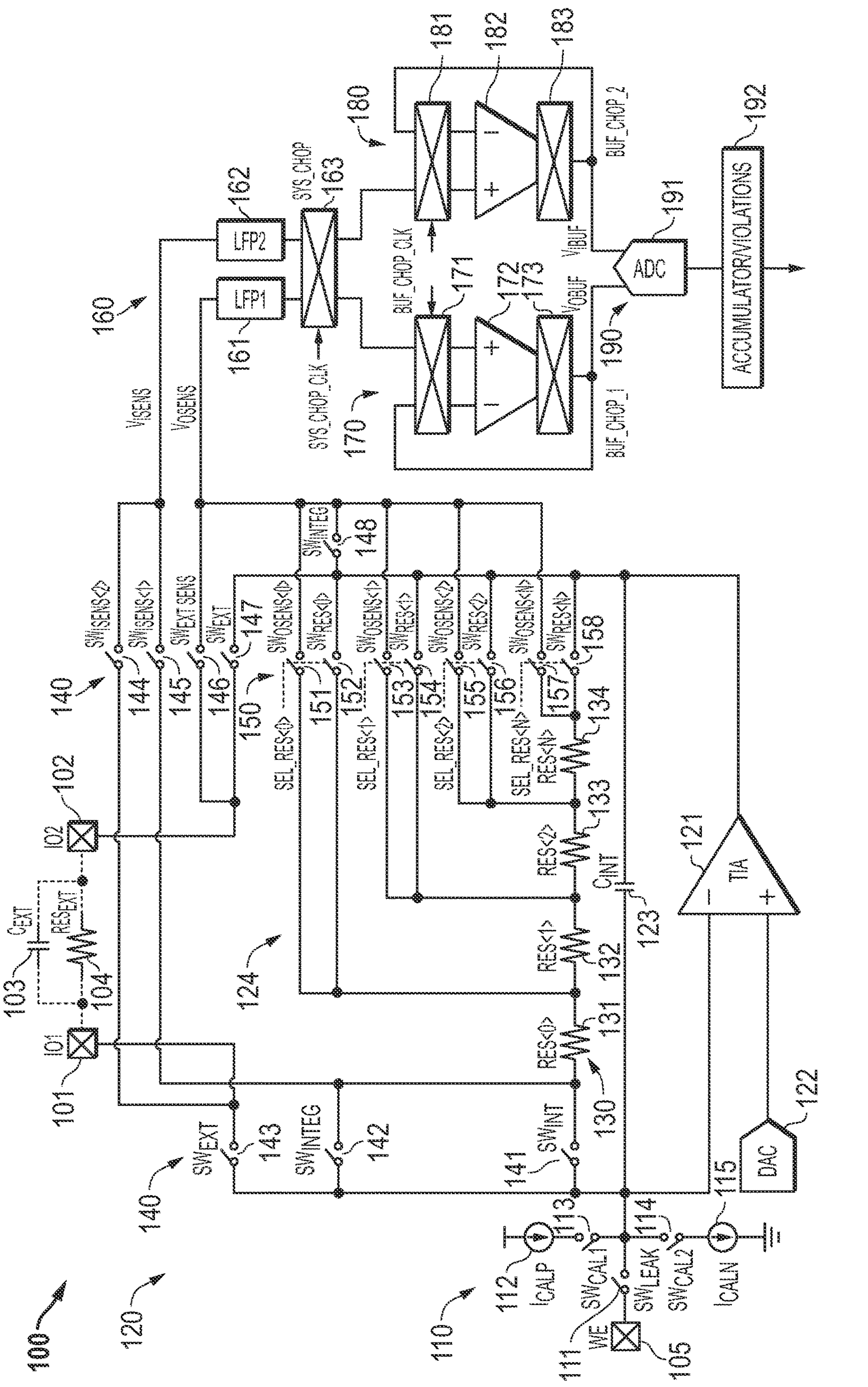
FIG. 1 illustrates in partial block diagram and partial schematic form a sensor circuit according to embodiments of the present disclosure.

FIG. 1 illustrates in partial block diagram and partial schematic form a sensor circuit 100 according to embodiments of the present disclosure. Sensor circuit 100 can be, for example, an electrochemical readout circuit used in a continuous glucose monitoring (CGM) device. Sensor circuit 100 includes generally a calibration circuit 110, an amplifier circuit 120, and a readout circuit 160. Sensor circuit 100 can be implemented as a monolithic integrated circuit, as discrete electrical components, or some combination of the two.

In FIG. 1, sensor circuit 100 is shown as an integrated circuit having an integrated circuit terminal 101, an integrated circuit terminal 102, and an integrated circuit terminal 105 conducting signals labelled "IO1", "IO2", and "WE" respectively. FIG. 1 also shows an external capacitor 103 and an external resistor 104 that are external to the integrated circuit and are optional. Capacitor 103 has a first terminal connected to integrated circuit terminal 101, and a second terminal connected to integrated circuit terminal 102, and has an associated capacitance labelled "$C_{EXT}$". Resistor 104 has a first terminal connected to integrated circuit terminal 101, and a second terminal connected to integrated circuit terminal 102, and has an associated resistance labelled "$RES_{EXT}$".

Calibration circuit 110 includes a switch 111, a current source 112, switches 113 and 114, and a current source 115. Switch 111 has a first terminal connected to integrated circuit terminal 105, and a second terminal, and is opened and closed by a signal labelled "$SW_{LEAK}$". Current source 112 has a first terminal connected to a power supply voltage terminal, and a second terminal. Switch 113 has a first terminal connected to the second terminal of current source 112, and a second terminal connected to the second terminal of switch 111, and is opened and closed by a signal labelled "$SW_{CAL1}$". Switch 114 has a first terminal connected to the second terminal of switch 113 and to the second terminal of switch 111, and a second terminal, and is opened and closed by a signal labelled "$SW_{CAL2}$". Current source 115 has a first terminal connected to the second terminal of switch 114, a second terminal connected to ground, and conducts a current labelled "$I_{CAL2N}$".

Amplifier circuit 120 includes a transimpedance amplifier 121 labelled "TIA", a digital-to-analog converter 122 labelled "DAC", a capacitor 123, and a variable resistor 124. Transimpedance amplifier 121 has a negative input connected to the second terminal of switch 111, a positive input, and an output. DAC 122 has an output connected to the positive input of transimpedance amplifier 121. Capacitor 123 has a first terminal connected to the output of transimpedance amplifier 121, and a second terminal connected to the negative input of transimpedance amplifier 121. Variable resistor 124 has a first terminal connected to the output of transimpedance amplifier 121, a second terminal connected to the negative input of transimpedance amplifier 121 through switch 141, and a control input for receiving a multi-bit control signal.

Variable resistor 124 includes a set of resistors 130, a set of mode select switches 140, and a set of resistance value switches 150. Resistors 130 and serially connected and include resistors 131, 132, 133, and 134. Resistor 131 has a first terminal, and a second terminal, and has an associated resistance labelled "RES<0>". Resistor 132 has a first terminal connected to the second terminal of resistor 131, and a second terminal, and has an associated resistance labelled "RES<1>". Resistor 133 has a first terminal connected to the second terminal of resistor 132, and a second terminal, and has an associated resistance labelled "RES<1>". Resistor 134 has a first terminal connected to the second terminal of resistor 133, and a second terminal, and has an associated resistance labelled "RES<n>". In the example shown in FIG. 1, n=4, but n can vary in various embodiments.

Mode select switches 140 include individual switches 141-147. Switch 141 has a first terminal connected to the second terminal of switch 111, a second terminal connected to the first terminal of resistor 131, and a control terminal for receiving a signal labelled "$SW_{INT}$". Switch 142 has a first terminal connected to the second terminal of switch 111, a second terminal connected to the first terminal of resistor 131, and a control terminal for receiving a signal labelled "$SW_{INTEG}$". Switch 143 has a first terminal connected to the second terminal of switch 111, a second terminal connected to integrated circuit terminal 101, and a control terminal for receiving a signal labelled "$SW_{EXT}$". Switch 144 has a first terminal connected to the second terminal of switch 143 and to integrated circuit terminal 101, a second terminal connected to node a node labelled "$V_{ISENS}$", and a control terminal for receiving a signal labelled "$SW_{ISENS<2>}$". Switch 145 has a first terminal connected to the first terminal of resistor 131 and the second terminals of switches 141 and 142, a second terminal connected to the second terminal of switch 144 at node $V_{INENS}$, and a control terminal for receiving a signal labelled "$SW_{ISENS<1>}$". Switch 146 has a first terminal connected to integrated circuit terminal 102, a second terminal connected to the second terminal of resistor 131, and a control terminal for receiving a signal labelled "$SW_{EXTSENS}$". Switch 147 has a first terminal connected to integrated circuit terminal 102, a second terminal connected to the output of transimpedance amplifier 121, and a control terminal for receiving control signal $SW_{EXT}$. Switch 148 has a first terminal connected to the second terminal of switch 147, a second terminal connected to node $V_{OSENS}$, and a control terminal for receiving control signal $SW_{INTEG}$.

Resistance value switches 150 includes representative switches 151-158. Switch 151 has a first terminal connected to the second terminal of resistor 131, a second terminal connected to node $V_{OSENS}$, and a control terminal for receiving a control signal labelled "$SW_{OSENS<0>}$". Switch 152 has a first terminal connected to the second terminal of resistor 131, a second terminal connected to the second terminal of switch 147, and a control terminal for receiving a control signal labelled "$SW_{RESS<0>}$". Switch 153 has a first terminal connected to the second terminal of resistor 132, a second terminal connected to node $V_{OSENS}$, and a control terminal for receiving a control signal labelled "$SW_{OSENS<1>}$". Switch 154 has a first terminal connected to the second terminal of resistor 132, a second terminal connected to the output of transimpedance amplifier 121, and a control terminal for receiving a control signal labelled "$SW_{RES<1>}$". Switch 155 has a first terminal connected to the second terminal of resistor 133, a second terminal connected to node $V_{OSENS}$, and a control terminal for receiving a control signal labelled "$SW_{OSENS<2>}$". Switch 156 has a first terminal connected to the second terminal of resistor 133, a second terminal connected to the output of transimpedance amplifier 121, and a control terminal for receiving a control signal labelled "$SW_{RES<2>}$". Switch 157 has a first terminal connected to the second terminal of resistor 134, a second terminal connected to node $V_{OSENS}$, and a control terminal for receiving a control signal labelled "$SW_{OSENS<n>}$". Switch 158 has a first terminal connected to the second terminal of resistor 134, a second terminal connected to the output of transimpedance amplifier 121, and a control terminal for receiving a control signal labelled "$SW_{OSENS<0>}$".

Readout circuit 160 includes a lowpass filter 161 labelled "LPF1", a lowpass filter 161 labelled "LPF2", a system chopping circuit 163, a chopper stabilized buffer 170, a chopper stabilized buffer 180, and a conversion stage 190. Lowpass filter 161 has an input connected to node $V_{OSENS}$, and an output. Lowpass filter 162 has an input connected to node $V_{ISENS}$, and an output. System chopping circuit 163 has a first input connected to the output of lowpass filter 161, a second input connected to the output of lowpass filter 162, a clock input for receiving a clock signal labelled "SYS-_CHOP_CLK", a first output, and a second output.

Chopper stabilized buffer 170 includes a buffer chopping circuit 171, an amplifier 172, and an output chop circuit 173. Buffer chopping circuit 171 has a first input, a second input connected to the first output of system chopping circuit 163, a clock input for receiving a clock signal labelled "BUF_CHOP_CLK", a first output, and a second output. Amplifier 172 has a negative input connected to the first output of buffer chopping circuit 171, a positive input connected to the second output of buffer chopping circuit 171, and first and second outputs (not shown). Differential-to-single ended converter 173 has a first input connected the first output of amplifier 172, a second input connected to the second output of amplifier 172, and an output connected to the first input of buffer chopping circuit 171 for providing a signal labelled "$V_{OBUF}$". Differential-to-single ended converter 173 has a first input connected the first output of amplifier 172, a second input connected to the second output of amplifier 172, and an output connected to the first input of buffer chopping circuit 171 for providing a signal labelled "$V_{OBUF}$".

Chopper stabilized buffer 180 includes a buffer chopping circuit 181, an amplifier 182, and an output chop circuit 183. Buffer chopping circuit 181 has a first input, a second input connected to the first output of system chopping circuit 163, a clock input for receiving the BUF_CHOP_CLK signal, a first output, and a second output. Amplifier 182 has a negative input connected to the first output of buffer chopping circuit 181, a positive input connected to the second output of buffer chopping circuit 181, and first and second outputs (not shown). Differential-to-single ended converter 183 has a first input connected the first output of amplifier 182, a second input connected to the second output of amplifier 182, and an output connected to the first input of buffer chopping circuit 181 for providing a signal labelled "$V_{OBUF}$". Differential-to-single ended converter 183 has a first input connected the first output of amplifier 182, a second input connected to the second output of amplifier 182, and an output connected to the first input of buffer chopping circuit 181 for providing a signal labelled "$V_{OBUF}$".

Conversion stage 190 includes an analog-to-digital converter 191 labelled "ADC", and a register 192 labelled "ACCUMULATOR/VIOLATIONS". Analog-to-digital converter 191 has a first input connected to node $V_{OBUF}$, a second input connected to node $V_{IBUF}$, and an output. Register 192 has an input connected to the output of analog-to-digital converter 191, and an output for providing a signal labelled "DIGITAL READOUT SIGNAL".

Sensor circuit 100 is useful as a sensor and readout circuit for applications such as CGM and similar products. In general, transimpedance amplifier 121 receives a reference voltage at its positive input from the output of digital-to-analog converter 122, and the closed loop feedback causes it to change its output voltage to make the voltage at the negative input equal to the reference voltage. Thus, the closed loop operation of amplifier circuit 120 maintains a reference voltage level on integrated circuit terminal 105. In some embodiments, transimpedance amplifier 121 is a class AB amplifier. During normal operation, switch 111 is closed, and thus the current into the sensor's work electrode (WE) is proportional to the resistance of the tissue, which is affected by the patient's glucose level. Since this current is changing only very slowly, the voltage drop across the resistors in resistors 130 is proportional to the patient's glucose level.

Sensor circuit 100 supports a variety of modes that allow its operation over a very large input current range and includes various features that overcome the limitations of known transimpedance amplifier sensor designs. In a calibration mode, switch 111 is open, and thus a calibration controller (not shown) can determine the input leakage current of transimpedance amplifier 121 using readout circuit 160.

In a normal operation mode, switch 111 is closed and switches 113 and 114 are open. Sensor circuit 100 further has an integration mode and a conversion mode. In the integration mode, transimpedance amplifier 121 is initialized by closing switches 141, 151, and 152 and keeping all other switches open. This configuration makes the feedback resistance equal to the value of resistor 131, which is the lowest resistance, or with other resistors as well. Switch 141 is then opened and switches 142 and 148 are closed, and sensor circuit 100 integrates the current into capacitor 123. Readout circuit 160 first samples the voltage across capacitor 123 ($V_1$) at time $t_1$. Readout circuit 160 next samples the voltage across capacitor 123 ($V_2$) at time $t_2$, in which $t_2$ is equal to a number of conversion clock cycles after $t_1$. These measurements allow the current into the WE electrode to be given as follows:

$$I_{WE} = \frac{V_2 - V_1}{nT_{CLK}} C_{INT} \quad [1]$$

By using integration mode, sensor circuit 100 can measure currents $I_{WE}$ in the pA range.

In the conversion mode, sensor circuit 100 measures the voltage across the feedback resistance, rather than using the known method of measuring the voltage between the output of transimpedance amplifier 121 and virtual ground, which in turn, cancel the non-linearity effect of the switches' resistances. In conversion mode, switch 141 is closed, switches 142-144 are open, and one of the SEL_RES<1:N> signals is active to close one of switch pairs 151/152, 153/154, 155/156, and 157/158 to set the feedback resistance to RES<0>, (RES<0>+RES<1>), (RES<0>+RES<1>+RES2<2>), or the sum of all the resistors, respectively, with all other ones of these switch pairs open. In conversion mode, the current into the WE electrode to be given as follows:

$$I_{WE} = \frac{V_{OBUF} - V_{IBUF}}{R} \quad [1]$$

Sensor circuit 100 also has an internal mode, in which capacitor 123 and selected ones of resistors 130 are connected between the output and negative input of transimpedance amplifier 121, and an external mode in which external capacitor 103 and external resistor 104 are used instead of the internal capacitance and resistance. In external mode, switches 143, 144, 146, and 147 are closed, and switches 141, 142, and 148 are open. While the internal resistances are not used to set the gain of transimpedance amplifier 121, switches 151-158 are preferably kept open to avoid adding unwanted capacitance to node $V_{OSENS}$.

In the conversion mode, sensor circuit 100 maintains high conversion linearity by measuring the voltage across the feedback resistance rather than the voltage between the output of transimpedance amplifier 121 and virtual ground. Thus, in internal resistance mode, sensor circuit 100 activates switch 145 to connect the first terminal of resistor 131 to $V_{ISENS}$ and a selected one of switch pairs 151/152, 153/154, 155/156, and 157/158 to connect to the second terminal of resistors 131, 132, 133, and 134, respectively. In external resistance mode, sensor circuit 100 activates switch 144 to connect the first terminal of external resistor 104 to $V_{ISENS}$ and switch 146 to connect the second terminal of external resistor 104 to $V_{OSENS}$.

Readout circuit 160 provides the DIGITAL READOUT SIGNAL based on the values of $V_{ISENS}$ and $V_{OSENS}$ at two points in time in integration mode, or at one point in time in conversion mode. Readout circuit 160, however, is able to provide good linearity and low noise by using signal chopping. Signal chopping can be performed on a differential signal by alternating the use of components such that any nonlinearity is applied uniformly to both true and complement versions of the differential signal. In this way, these non-linearities average out to zero.

Readout circuit 160 performs a two-level chopping technique. First, system chopping circuit 163 chops the output of lowpass filters 161 and 162 by swapping the signal paths synchronously with the SYS_CHOP_CLK. System chopping circuit 163 is used to cancel the offset caused by analog-to-digital converter 191. Second, chopper stabilized buffers 170 and 180 perform further chopping to cancel the offset on the buffered voltage across the resistance between the output and negative input of transimpedance amplifier 121.

The voltages at the terminals of the feedback resistance of transimpedance amplifier 121 are input to lowpass filters 161 and 162, respectively, followed by a system chopping circuit 163. The output of system chopping circuit 163 is input to two chopper stabilized buffers 170 and 180. System chopping circuit 163 cancels the offset of analog-to-digital converter 191, while chopper stabilized buffers 170 and 180 cancel the offset on the buffered voltage across the resistance of transimpedance amplifier 121. Sensing the voltage across the resistance of transimpedance amplifier 121, chopping using system chopper 163, and buffering using chopper stabilized buffers 170 and 180 substantially cancel the voltage offset without injecting charge on the WE pin, which is done by some known transimpedance amplifier implementations. Sensor circuit 100 uses readout circuit 160 having system chopper 163 and buffer choppers 173 and 183 to achieve low offset and low noise, but other low-offset, low-noise buffers can be used instead.

Sensor circuit 100 provides various advantages over known TIA-based designs. First, it provides bidirectional current measurement.

Second, it provides a wide input current range, e.g., from pA to μA, with high accuracy. It uses a variable gain transimpedance amplifier whose gain can be set using selectable resistances. The accuracy can be improved by adding more resistances that are selectively switched. Also, it provides an integration mode to accommodate very small currents by sensing the small currents over multiple clock cycles.

Third, it provides high conversion linearity by providing sensing switches to measure the voltage across the feedback resistance (in linear mode) or capacitor (in integration mode) instead of measuring the output of the transimpedance amplifier with respect to virtual ground. In some embodiments, silicon-chromium (SiCr) resistors can be used as resistors 130 to provide low conversion temperature drift.

Fourth, it provides accurate calibration using two low temperature coefficient current sources.

Fifth, it provides the ability to switch between internal and external resistances without affecting the conversion linearity.

Sixth, it provides offset cancellation and noise reduction by using a readout circuit that measures the voltage across the transimpedance amplifier feedback resistance using chopper-stabilized buffers, and further by using a system chopper to cancel offset between system chopper 163 and the output of analog-to-digital converter 191. In addition in some embodiments, it uses low noise, low leakage metal-oxide-semiconductor (MOS) T-switches for resistance value switches 150.

Seventh, it provides a sensor disconnect switch to measure leakage in the sense node.

Figure 2:
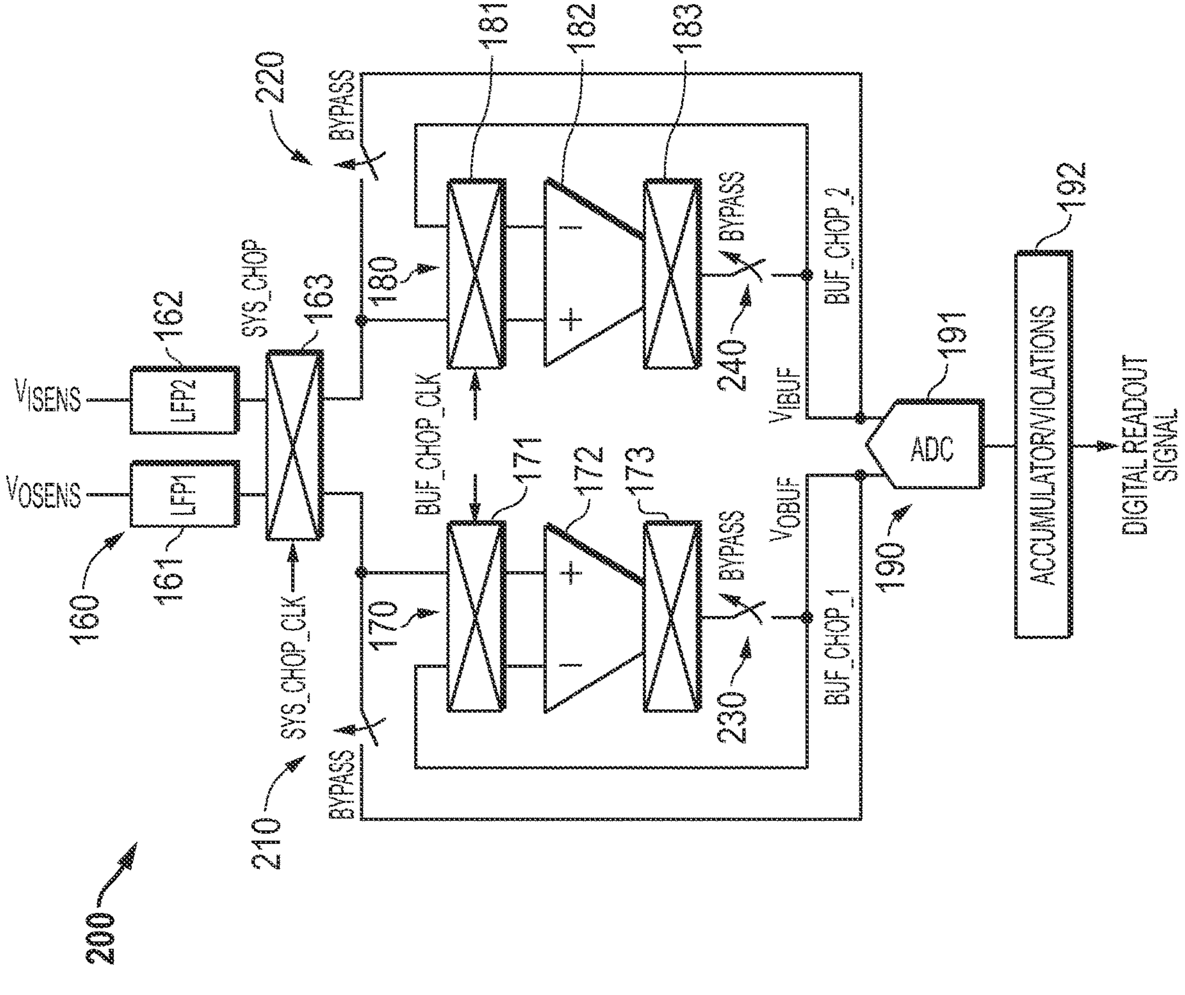
FIG. 2 illustrates in partial block diagram and partial schematic form a readout circuit that can be used instead of the readout circuit of FIG. 1 according to embodiments of the present disclosure.

FIG. 2 illustrates in partial block diagram and partial schematic form a readout circuit 200 that can be used instead of readout circuit 160 of FIG. 1 according to embodiments of the present disclosure. Readout circuit 200 includes the same elements as readout circuit 160, but includes bypass paths to selectively bypass chopper stabilized buffers 170 and 180. To accomplish this feature, readout circuit 200 includes switches 210, 220, 230, and 240. Switch 210 has a first terminal connected to the first output of system chopping circuit 163, a second terminal connected to the first input of analog-to-digital converter 191, and is closed in response to a signal labelled "BYPASS" being active at a logic high voltage, and opened in response the BYPASS signal being inactive at a logic low voltage. Switch 220 has a first terminal connected to the second output of system chopping circuit 163, a second terminal connected to the second input of analog-to-digital converter 191, and is closed in response to the BYPASS signal being active at a logic high voltage, and opened in response the BYPASS signal being inactive at a logic low voltage. Switch 230 has a first terminal connected to the output of differential-to-single ended converter 173, a second terminal connected to the first input of analog-to-digital converter 191, and is opened in response to the BYPASS signal being active at a logic high voltage, and closed in response the BYPASS signal being inactive at a logic low voltage. Switch 240 has a first terminal connected to the output of differential-to-single ended converter 183, a second terminal connected to the second input of analog-to-digital converter 191, and is opened in response to the BYPASS signal being active at a logic high voltage, and closed in response the BYPASS signal being inactive at a logic low voltage. Readout circuit 200 provides the programmable use or bypass of chopper stabilized buffers 170 and 180 based on the needs of the particular application. For example, systems that require higher accuracy can de-activate the BYPASS signal at a logic low to provide the better accuracy using buffer chopping, and can activate the BYPASS signal at a logic high to reduce power consumption and increase battery life for systems that have adequate accuracy. In the latter case, readout circuit 200 would also include power supply switches, not shown in FIG. 2, to reduce bias and leakage power consumption. In general, readout circuit 200 further illustrates how the various features of sensor circuit 100 can be used selectively and independently either by design or programmably.

The above-disclosed subject matter is to be considered illustrative, and not restrictive, and the appended claims are intended to cover all such modifications, enhancements, and other embodiments that fall within the scope of the claims. For example, different combinations of the disclosed features can be used in different embodiments to achieve some of the benefits discussed herein. Moreover, the various features can be used selectively and independently either by design or programmably. Also, sensor circuit 100 can be used as a sensor circuit in other applications besides electrochemical readout or CGM. In the illustrated embodiment, sensor circuit 100 used a readout circuit 160 using a system chopper and buffer choppers to achieve low offset and low noise. In other embodiments, other circuits can be used to achieve low offset and low noise. The number if switches and resistors used to form resistance 124 can also vary in different embodiments.

Thus, to the maximum extent allowed by law, the scope of the present invention is to be determined by the broadest permissible interpretation of the following claims and their equivalents, and shall not be restricted or limited by the forgoing detailed description.

What is claimed is:

1. A sensor circuit, comprising:

a transimpedance amplifier having a first input for receiving a measured signal, a second input for receiving a reference signal, and an output;

a feedback network comprising a capacitor and a variable resistor each coupled between said output and said first input of said transimpedance amplifier; and a readout circuit coupled to said feedback network and having an output for providing a readout signal;

wherein in a conversion mode, said readout circuit provides said readout signal based on one sample of said output of said transimpedance amplifier; and wherein in an integration mode, said readout circuit provides said readout signal based on a plurality of samples of said output of said transimpedance amplifier.

2. The sensor circuit of claim 1, wherein:

said variable resistor comprises a plurality of serially coupled resistors selectively switched between a current sense node and an output sense node; and said readout circuit has a first input coupled to said current sense node, and a second input coupled to said output sense node.

3. The sensor circuit of claim 2, wherein:

said plurality of serially coupled resistors are selectively switched between said current sense node and said output sense node using a plurality of low-leakage switches.

4. The sensor circuit of claim 2, wherein:

in said conversion mode, said feedback network couples outputs of selected ones of said plurality of serially coupled resistors to said current sense node and said output sense node; and in said integration mode, said feedback network couples a first terminal of said capacitor to said current sense node and a second terminal of said capacitor to said output sense node.

5. The sensor circuit of claim 2, wherein said feedback network is implemented on a monolithic integrated circuit, and said monolithic integrated circuit further comprises:

a first integrated circuit terminal coupled to said current sense node; and a second integrated circuit terminal coupled to said output sense node, wherein:

in an internal resistance mode, said feedback network couples said variable resistor between said current sense node and said output sense node and decouples said first integrated circuit terminal from said current sense node and said second integrated circuit terminal from said output sense node; and in an external resistance mode, said feedback network couples said first integrated circuit terminal to said current sense node and said second integrated circuit terminal to said output sense node and decouples said variable resistor from said current sense node and said output sense node.

6. The sensor circuit of claim 2, wherein:

said plurality of serially coupled resistors comprise silicon-chromium (SiCr) resistors.

7. The sensor circuit of claim 1, wherein said readout circuit comprises at least one low-noise and low-offset stage.

8. The sensor circuit of claim 7, wherein said readout circuit comprises:

a chopper stabilized input stage for providing a voltage on first and second buffered output nodes; and a conversion stage having inputs coupled to said first and second buffered output nodes, and an output for providing a digital readout signal.

9. The sensor circuit of claim 8, wherein said conversion stage comprises:

an analog-to-digital converter having first and second inputs coupled to said first and second buffered output nodes, respectively, and an output; and an accumulator stage having an input coupled to said output of said analog-to-digital converter, and an output for providing said digital readout signal, wherein in said integration mode, said accumulator stage provides said readout signal based on a plurality of outputs of said analog-to-digital converter.

10. The sensor circuit of claim 1, wherein:

said feedback network comprises a capacitor and a variable resistor each coupled between said output and said first input of said transimpedance amplifier, wherein said feedback network forms an output signal on a current sense node and an output sense node; and said readout circuit is coupled to said current sense node and said output sense node and comprises at least one low-noise and low-offset stage.

11. The sensor circuit of claim 10, wherein said readout circuit uses chopper stabilization to provide said readout signal.

12. The sensor circuit of claim 11, wherein said readout circuit comprises:

a system chopping circuit having a first input coupled to said output sense node, a second input coupled to said current sense node, a clock input for receiving a system chop clock signal, and first and second outputs;

a first buffer having an input coupled to said first output of said system chopping circuit, and an output;

a second buffer having an input coupled to said second output of said system chopping circuit, and an output; and a conversion stage having inputs coupled to said output of said first buffer and said output of said second buffer, respectively, and an output for providing a digital readout signal.

13. The sensor circuit of claim 12, wherein:

said first input of said system chopping circuit is coupled to said output sense node through a first lowpass filter; and said second input of said system chopping circuit is coupled to said current sense node through a second lowpass filter.

14. The sensor circuit of claim 12, wherein said conversion stage comprises:

an analog-to-digital converter having first and second inputs coupled to said output of said first buffer and said output of said second buffer, respectively. and an output; and an accumulator stage having an input coupled to said output of said analog-to-digital converter, and an output for providing said digital readout signal.

15. The sensor circuit of claim 14, wherein:

in a conversion mode, said accumulator stage provides said digital readout signal in response to one sample of said output of said analog-to-digital converter; and in an integration mode, said accumulator stage provides said digital readout signal in response to a plurality of samples of said output of said analog-to-digital converter.

16. The sensor circuit of claim 15, wherein in said integration mode, said analog-to-digital converter monitors each of said plurality of samples of said output of said first buffer and said second buffer, and detects a saturation condition in response to an output of at least one of said first buffer and said second buffer exceeding a threshold.

17. The sensor circuit of claim 10, further comprising:

a calibration circuit coupled to said first input of said transimpedance amplifier, for measuring leakage current at said first input of said transimpedance amplifier.

18. A method of reading out a condition of a sensor, comprising:

converting a current conducted by the sensor into a voltage using a transimpedance amplifier having a first input adapted to be coupled to the sensor;

forming a voltage using a feedback network comprising a capacitor and a resistor each coupled between an output and said first input of said transimpedance amplifier;

in a conversion mode, measuring a voltage across said resistor and providing a readout signal based on one sample of said voltage across said resistor; and in an integration mode, measuring a voltage across said capacitor and providing said readout signal based on a plurality of samples of said voltage across said capacitor.

19. The method of claim 18, wherein said resistor comprises a variable resistor and said forming said voltage comprises:

varying a resistance of said variable resistor based on a desired current range of the sensor.

20. The method of claim 19, wherein varying said resistance of said variable resistor comprises:

selectively coupling an external resistor between said output and said first input of said transimpedance amplifier.

21. The method of claim 18, wherein providing said readout signal comprises:

converting a selected one of said voltage across said resistor and said voltage across said capacitor into a digital signal, thereby forming a digital readout signal.

* * * * *